United States Patent
Mahaffey, Jr.

Patent Number: 5,918,269
Date of Patent: Jun. 29, 1999

[54] NAPHTHALIMIDE COLORANTS WITH IMPROVED COMPATIBILITY IN REFRIGERATION AND AIR CONDITIONING LUBRICANTS

[75] Inventor: Robert L. Mahaffey, Jr., Spartanburg, S.C.

[73] Assignee: Milliken & Company, Spartanburg, S.C.

[21] Appl. No.: 09/025,201

[22] Filed: Feb. 18, 1998

[51] Int. Cl.$^6$ .......................... G01M 3/04; G01N 21/64; C09K 11/06; C07D 221/14
[52] U.S. Cl. .................. 73/40.7; 73/40.5 R; 252/301.26; 546/100
[58] Field of Search .................. 546/100; 73/40.5 R, 73/40.7; 252/301.26

[56] References Cited

U.S. PATENT DOCUMENTS

| | | | |
|---|---|---|---|
| Re. 35,370 | 11/1996 | Henry | 73/40.7 |
| Re. 35,395 | 12/1996 | Henry | 73/40.7 |
| 2,074,288 | 3/1937 | Tinker et al. | 87/9 |
| 2,096,099 | 10/1937 | Gaugler | 73/51 |
| 2,205,408 | 6/1940 | Hopff et al. | 87/9 |
| 2,385,106 | 9/1945 | Scalera et al. | 546/100 |
| 2,434,448 | 1/1948 | Wade | 62/170 |
| 3,147,264 | 9/1964 | Klein | 260/281 |
| 3,770,640 | 11/1973 | Bartlett | 252/68 |
| 3,900,287 | 8/1975 | Jackson | 8/174 |
| 4,170,564 | 10/1979 | Brendle | 252/68 |
| 4,662,940 | 5/1987 | Monier | 106/33 |
| 4,758,366 | 7/1988 | Parekh | 252/68 |
| 4,897,551 | 1/1990 | Gersh et al. | 250/461.1 |
| 5,149,453 | 9/1992 | Parekh | 252/68 |
| 5,357,782 | 10/1994 | Henry | 73/40.7 |
| 5,389,302 | 2/1995 | Warren, Jr. | 252/408.1 |
| 5,420,136 | 5/1995 | Lewis et al. | 514/296 |
| 5,421,192 | 6/1995 | Henry | 73/40.7 |
| 5,440,919 | 8/1995 | Cooper | 73/40.7 |
| 5,574,213 | 11/1996 | Shanley | 73/40.7 |
| 5,681,984 | 10/1997 | Cavestri et al. | 73/40.7 |

*Primary Examiner*—Bernard Dentz
*Attorney, Agent, or Firm*—Terry T. Moyer; William S. Parks

[57] ABSTRACT

Novel naphthalimide-derivative colorants are provided which are present in a neat liquid state at ambient temperature and pressure. Such colorants are produced through the reaction between 4-chloro (or bromo)-1,8 naphthalic anhydride and at least one etheramine, at least one branched alkylamine, or mixtures thereof. The inventive colorants are excellent leak detection agents for refrigeration and air conditioning systems. These naphthalimide derivatives are completely miscible in all different types of standard refrigeration and air conditioning lubricants. Furthermore, since these colorants are liquid, they are not susceptible to crystallizing within such systems. Thus, the inventive naphthalimide leak detecting agents cannot cause the failure of such machinery due to the crystallization of colorant and subsequent clogging of system compressors. Methods of making and using such inventive naphthalimide-derivative colorants are also disclosed.

11 Claims, No Drawings

NAPHTHALIMIDE COLORANTS WITH IMPROVED COMPATIBILITY IN REFRIGERATION AND AIR CONDITIONING LUBRICANTS

FIELD OF THE INVENTION

This invention relates to improved liquid aminonaphthalimide colorants and their use as leak detection colorants in refrigeration and air conditioning systems. These colorants are derived from 4-chloro(or bromo)-1,8-naphthalic anhydride and either etheramines or branched alkylamines. Specific methods of making such colorants are also contemplated within this invention.

DISCUSSION OF THE PRIOR ART

Naphthalimide colorants are well known as leak detection agents within refrigeration and air conditioning systems. Such systems contain refrigerant, etc., compositions which comprise compressible gases and lubricants. The lubricants are present in order to prevent wear to the internal parts of such a refrigeration or air conditioning system. Prior patents disclosing such leak detecting colorants include U.S. Pat. Nos. 4,758,366, to Parekh, which mentions naphthalimides, although patentee does not correctly describe their structure, and U.S. Pat. No. 5,421,192, to Henry, which broadly teaches naphthalamides. Such colorants are generally incorporated within mineral oil or other classes of lubricants necessarily added to refrigerants and refrigerant azeotropes. If a leak exists within the pertinent system, a portion of the lubricant, including the solubilized colorant, would also transport out of the system. Naphthalimides permit easy detection of such leaks due to their ability to fluoresce under ultraviolet light. Generally, a light source within the ultra- or near ultraviolet spectrum is shone in the direction of a suspected leak and, if a leak exists, the naphthalimide colorant fluoresces a yellow-green hue.

The principle shortcomings of the previously disclosed naphthalimide colorants have been their low solubility within and low degree of compatibility with standard refrigeration and air conditioning system lubricants. It has been discovered that quite often the employed naphthalimide-based compound precipitates or crystallizes within the standard lubricant causing clogs within the orifices of the system compressor. This problem causes wear on the internal parts of the system, eventually rendering the entire system inoperable. An improved, non-crystallizing, yet effectively fluorescing colorant for leak detection is thus necessary within the refrigeration, air conditioning, etc., industry.

DESCRIPTION OF THE INVENTION

It is thus an object of the invention to provide a naphthalimide-derivative colorant which is liquid in its pure form at ambient temperature and pressure. A further object of the invention is to provide a liquid naphthalimide-derivative colorant which is extremely soluble in and highly compatible with all classes of refrigeration and air conditioning system lubricants. Another object of the invention is to provide a fluorescent to facilitate leak detection for the refrigeration and air conditioning industries. Yet another object of this invention is to provide a process for making such an improved fluorescent naphthalimide-derivative colorant.

Accordingly, this invention provides a naphthalimide derivative which is liquid at ambient temperature and pressure. By the term ambient, it is meant from between 20° and 30° C. and from about 0.75 to about 1.25 atmospheres. In actuality, the inventive colorant will remain in a liquid state at all times, even upon introduction into a refrigeration or air conditioning system. Upon such an introduction, the colorant immediately solubilizes within any liquid lubricant or lubricant-refrigerant mixture within the system. A minimum amount of agitation and time is required for the inventive naphthalimide to dissolve within the lubricant. As such, there is no opportunity for the colorant to precipitate from solution or crystallize within the system. Thus, the operation of the refrigeration or air conditioning system is not endangered to any degree merely from the above-described incorporation of the inventive colorant.

The specific structure of the inventive colorant is provided in Figure (I):

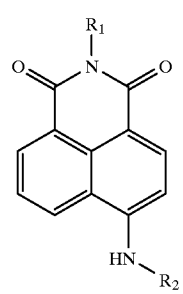

(I)

wherein $R_1$ and $R_2$ are, either the same or different, $C_1$–$C_{30}$ unbranched or $C_3$–$C_{30}$ branched alkoxypropyl, α- or β-$C_3$–$C_{30}$ branched alkyl, or $C_3$–$C_{30}$ unbranched alkyl, wherein only one of $R_1$ or $R_2$ can be $C_3$–$C_{30}$ unbranched alkyl. These colorants are the product of a displacement reaction between 4-chloro or bromo-1,8 naphthalic anhydride and at least one etheramine or at least one branched alkylamine, or mixtures thereof, such that the resultant products are within the structure in Figure (I), above. The particularly preferred etheramines have the molecular formula provided in Figure (II):

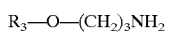

$$R_3\text{—}O\text{—}(CH_2)_3NH_2 \qquad (II)$$

wherein $R_3$ is a $C_1$–$C_{30}$ branched or unbranched alkyl group. The specific preferred branched alkylamines are primary amines with branches located in the α or β position relative to the nitrogen atom.

The liquid state of the inventive colorants is achieved through the addition of atoms within the alkyl chain moieties which substantially prevent crystallization of the naphthalimide derivatives. For instance, and merely within one embodiment of the invention, the reaction of at least one etheramine with 4-halo-1,8-naphthalic anhydride produces an alkyl moiety in the N-, 4-, or both the N- and 4-position, including a hetero atom, preferably oxygen. The presence of such a hetero atom disrupts the regularity of the repeating methylene units within the alkyl chain and thus prevents the molecule from crystallizing. In another embodiment, an etheramine reactant includes a secondary or tertiary alkyl moiety which produces such a branched alkyl chain on the naphthalimide derivative product. Such a structure sterically binders the ability of the compound from crystallizing. Furthermore, in yet another embodiment of the invention, both a hetero atom and a branched alkyl moiety are added to the naphthalic anhydride to form a liquid naphthalimide-derivative leak detecting colorant. These particular descriptions are, again, merely embodiments of the invention and are not intended to limit the scope of the present invention in any way.

The potential lubricants contemplated within this invention are limitless. The colorant appears to dissolve easily within all the standard refrigerant and air conditioning lubricants. These include classes such as naphthenic oils, paraffinic oils, alkylbenzenes, polyalkylene glycols (particularly polypropylene glycol), silicones, di- and tri-esters of di- and tri-carboxylic acids, polyalkyl silicate oils, and polyol esters. The refrigerants in which the lubricant/colorant combination is added include those which are standard within the art. Included in this class are hydrofluorocarbons, hydrochlorofluorocarbons, and other polyhalogenated hydrocarbons. More particular suitable refrigerants and air conditioning agents are disclosed within the Parekh reference, U.S. Pat. No. 4,758,366, and the Henry reference, U.S. Pat. No. 5,421,192, supra.

The method followed in introducing the inventive colorants within refrigeration and/or air conditioning systems is as follows:

First, the colorant and the lubricant are mixed, in ratios of amounts of from about 0.0001 to about 0.1 grams of colorant for every about 100 grams of lubricant. Generally, the amount required for each different type of inventive liquid naphthalimide-derivative colorant will differ due to the different possible structures. Some of the colorants require as little as 0.0001 grams per 100 grams of lubricant to provide effective leak detection; others require more.

Second, the colorant/lubricant mixture is introduced within either a refrigeration system composition comprising a refrigerant composition, or an air conditioning system comprising a halogenated hydrocarbon. Generally, the weight ratio of the lubricant to refrigerant is from about 1:3 to about 1:100.

Third, the system is operated a sufficient time for proper mixing of the colorant/lubricant mixture within the refrigerant composition of the refrigeration system and the halogenated hydrocarbon composition of the air conditioning system. Generally, the required time is of very short duration since the lubricants are miscible within the refrigerant/halogenated hydrocarbon and the liquid colorant does not alter such a solubility.

Finally, the presence of a leak in the system can be determined by directing an ultraviolet light at the system and subsequently detecting a fluorescing color through visual observation of the lighted area. If a leak exists, the colorant should fluoresce a yellow-green hue under such an ultraviolet light source (about 365 nm in wavelength).

Because the naphthalimides of the present invention are miscible within all classes of lubricants, extremely concentrated solutions can be produced within the lubricant which thus serves, basically, as a solvent or carrier for the inventive colorant. Beneficially, then, only a small amount of the colorant is needed to effectively provide sufficient leak detection agents within refrigeration and/or air conditioning systems. This translates into lower cost for the consumer since lower amounts of relatively expensive leak detection colorant would be necessary. Alternatively, since the inventive colorant is a liquid, it can easily be added in a neat state, without the need for a solvent or carrier. Again, this alternative further reduces the necessary amount of the leak detection formulation added to the refrigeration and/or air conditioning system.

Previous attempts have been made in the prior art to increase the solubility and improve the compatibility of such naphthalimide leak detection colorants with the standard refrigerant lubricants. The methods followed solely pertained to the varying of the chain lengths of the alkyl moieties, such as discussed below in EXAMPLEs 6 and 7 as well as with the colorant marketed as Day Glo 100™, also tested below. Such colorants are not present in a liquid state, and thus are still prone to crystallization within refrigerant and/or air conditioning systems.

DESCRIPTION OF THE PREFERRED EMBODIMENT

The following examples are indicative of the preferred embodiments, both the compositions and methods, of this invention:

EXAMPLE 1

Synthesis of N-hexyloxypropyl-4-hexyloxypropylamino-1,8-naphthalimide 182.0 grams of hexyloxypropylamine (available from Tomah, Inc. as PA-10) was placed in a flask to which 116.3 grams of 4-chloro-1,8-naphthalic anhydride and 26.5 grams of sodium carbonate was added. The mixture was heated at 130° C. for one hour, after which the temperature was raised to 160° C. and the mixture was subsequently heated for eight more hours. The mixture was then cooled, washed with water, and dried under vacuum. The product was a viscous liquid having a maximum absorbance in methanol at 441 nm and a color value of 26.1.

EXAMPLE 2

Synthesis of N-(2-ethylhexyloxypropyl)-4-(2-ethylhexyloxypropylamino)-1,8-naphthalimide The same basic procedure as in EXAMPLE 1 was followed except that an equivalent molar amount of 2-ethylhexyloxypropylamine was substituted for hexyloxypropylamine. The resultant product was a viscous liquid with a maximum absorbance in methanol at 442 nm and a color value of 22.6.

EXAMPLE 3

Synthesis of N-hexadecyloxypropyl-4-hexadecyloxypropylamino-1,8-naphthalimide

The same basic procedure as in EXAMPLE 1 was followed except that an equivalent molar amount of 2-hexadecyloxypropylamine was substituted for hexyloxypropylamine. The resulting product was a viscous liquid with a maximum absorbance in toluene at 423 nm and a color value of 15.1.

EXAMPLE 4

Synthesis of N-alkyloxypropyl-4-alkyloxypropylamino-1,8-naphthalimide Using a Mixture of Amines The same basic procedure as in EXAMPLE 1 was followed except that an equivalent molar amount each of hexyloxypropylamine and 2-ethylhexyloxypropylamine was substituted for hexyloxypropylamine. The resulting product was a viscous liquid with a maximum absorbance at 442 nm and a color value of 25.0.

EXAMPLE 5

Synthesis of N-(2-ethylhexyl)-4-(2-ethylhexylamino)-1,8-naphthalimide

The same basic procedure as in EXAMPLE 1 was followed except that an equivalent molar amount of 2-ethylhexylamine was substituted for hexyloxypropylamine. The resulting product was a viscous liquid with a maximum absorbance in methanol at 444.5 nm and a color value of 27.4.

EXAMPLE 6 (COMPARATIVE)

Synthesis of N-octyl-4-octylamino-1,8-naphthalimide 38.1 grams of 4-chloro-1,8-naphthalic anhydride (61% pure) was placed in a flask to which 27.1 grams of octylamine and 5.3 grams of sodium carbonate. The mixture was gradually heated to 160° C. for eight hours. After cooling, water and dilute hydrochloric acid were added. The resultant product was a precipitate which was collected by filtration and dried. The solid product had a melting point of 86–87° C., a maximum absorbance at 443 nm in methanol, and a color value of 34.2.

EXAMPLE 7 (COMPARATIVE)

Synthesis of N-decyl-4-decylamino-1,8-naphthalimide

The same basic procedure as in EXAMPLE 6 was followed except that 33.0 grams of decylamine was substituted for octylamine. The resultant product had a melting point of 92–94° C., a maximum absorbance at 443 nm in methanol and color value of 30.9.

Each product of the seven EXAMPLEs was mixed with four separate common refrigeration or air conditioning lubricants in order to perform limiting solubility comparisons. The mixing and measuring for each colorant was performed in exactly the same manner. The degree of miscibility is noted for each colorant with the term Miscible representing complete solubility and numbers representing specific, incremental measurements.

TABLE

| Lubricant | Colorants from Examples | | | | | | | Day Glo 100 ™[1] |
|---|---|---|---|---|---|---|---|---|
|  | 1 | 2 | 3 | 4 | 5 | 6 | 7 |  |
| Mineral Oil[2] | Miscible | Miscible | Miscible | Miscible | Miscible | <0.5% | <0.5% | <2.0% |
| Polyol Ester[3] | Miscible | Miscible | Miscible | Miscible | Miscible | <0.5% | <0.5% | <0.5% |
| PAG Oil[4] | Miscible | Miscible | Miscible | Miscible | Miscible | <0.5% | <0.5% | <5.0% |
| Alkyl Benzene[5] | Miscible | Miscible | Miscible | Miscible | Miscible | <2.0% | <0.5% | <7.5% |

[1] N-butyl-4-butylamino-1,8-naphthalimide colorant manufactured by Day Glo Corporation
[2] Hydrocal 45, a product of Calumet Lubricants Co.
[3] Solest 22, a product of CPI Engineering, Inc.
[4] BVA-150, a product of B-V Associates, Inc.
[5] Zerol 150, a product of Shrieve Chemical Products, Inc.

From these comparisons, the inventive naphthalimide-derivative liquid colorants provide complete miscibility within the standard refrigeration and air conditioning lubricants. As a result, there are no potential problems with crystallization and ultimate clogging of machinery parts within any such systems in which the inventive colorants are utilized.

There are, of course, many alternative embodiments and modifications of the present invention which are intended to be included within the spirit and scope of the following claims.

What I claim is:

1. A naphthalimide-derivative colorant which is present in a neat liquid state at ambient temperature and pressure wherein
said colorant is the reaction product of 4-halo-1,8-naphthalic anhydride and a reactant selected from the group consisting of at least one etheramine.

2. The colorant of claim 1 wherein
said 4-halo-1,8-naphthalic anhydride is selected from the group consisting of 4-chloro-1,8-naphthalic anhydride and 4-bromo-1,8-naphthalic anhydride; and
said at least one etheramine is represented by the formula (II)

$$R_3\text{—}O\text{—}(CH_2)_3NH_2 \qquad (II)$$

wherein
$R_3$ is a ($C_1$–$C_{30}$ branched or unbranched) alkyl group.

3. A leak detecting composition for a refrigeration or air conditioning system comprising:
at least one lubricant, and
at least one naphthalimide-derivative colorant which is present in a neat liquid state at ambient temperature and pressure wherein
said colorant is the reaction product of 4-halo-1,8-naphthalic anhydride and a reactant selected from the group consisting of at least one etheramine.

4. The leak detecting composition of claim 3 wherein
said 4-halo-1,8-naphthalic anhydride is selected from the group consisting of 4-chloro-1,8-naphthalic anhydride and 4-bromo-1,8-naphthalic anhydride; and
said at least one etheramine is represented by the formula (II)

$$R_3\text{—}O\text{—}(CH_2)_3NH_3 \qquad (II)$$

wherein
$R_3$ is a ($C_1$–$C_{30}$ branched or unbranched) alkyl group.

5. A method for detecting leaks in a refrigeration system comprising the steps of
(a) introducing at least a leak detecting amount of a naphthalimide-derivative colorant which is present in a neat liquid state at ambient temperature and pressure, wherein said colorant is the reaction product of 4-halo-1,8-naphthalic anhydride and a reactant selected from the group consisting of at least one etheramine, within a lubricant to form a colorant/lubricant mixture;
(b) introducing said colorant/lubricant mixture within a refrigeration system composition comprising a refrigerant composition;

(c) operating said system for a sufficient time to allow thorough mixing of said colorant/lubricant mixture and said refrigerant composition; and (d) determining the presence of a leak in said system by directing an ultraviolet light at said system and subsequently detecting a fluorescent color through visual observation.

6. The method of claim 5 wherein said 4-halo-1,8-naphthalic anhydride is selected from the group consisting of 4-chloro-1,8-naphthalic anhydride and 4-bromo-1,8-naphthalic anhydride; and said at least one etheramine is represented by the formula (II)

$$R_3\text{—}O\text{—}(CH_2)_3NH_2 \qquad (II)$$

wherein $R_3$ is a ($C_1$–$C_{30}$ branched or unbranched) alkyl group.

7. A method for detecting leaks in an air conditioning system comprising the steps of (a) introducing at least a leak detecting amount of a naphthalimide-derivative colorant which is present in a neat liquid state at ambient temperature and pressure, wherein said colorant is the reaction product of 4-halo-1,8-naphthalic anhydride and a reactant selected from the group consisting of at least one etheramine, within a lubricant to form a colorant/lubricant mixture;

(b) introducing said colorant/lubricant mixture within an air conditioning system composition comprising a halogenated hydrocarbon composition;

(c) operating said system for a sufficient time to allow thorough mixing of said colorant/lubricant mixture and said halogenated hydrocarbon composition; and (d) determining the presence of a leak in said system by directing an ultraviolet light at said system and subsequently detecting a fluorescent color through visual observation.

8. The method of claim 7 wherein said 4-halo-1,8-naphthalic anhydride is selected from the group consisting of 4-chloro-1,8-naphthalic anhydride and 4-bromo-1,8-naphthalic anhydride; and said at least one etheramine is represented by the formula (II)

$$R_3\text{—}O\text{—}(CH_2)_3NH_2 \qquad (II)$$

wherein $R_3$ is a ($C_1$–$C_{30}$ branched or unbranched) alkyl group.

9. A method of making a naphthalimide-derivative colorant, which is present in a neat liquid state at ambient temperature and pressure, comprising the steps of (a) reacting a 4-halo-1,8-naphthalic anhydride with at least one etheramine;

(b) heating the mixture to at most 160° C.;

(c) cooling the mixture;

(e) washing the mixture; and (f) drying the mixture under a vacuum.

10. The method of claim 9 wherein said 4-halo-1,8-naphthalic anhydride is 4-chloro-1,8-naphthalic anhydride and wherein said at least one etheramine is represented by the formula (II):

$$R_3\text{—}O\text{—}(CH_2)_3NH_2 \qquad (II)$$

wherein $R_3$ is a ($C_1$–$C_{30}$ branched or unbranched) alkyl group.

11. The method of claim 9 wherein said 4-halo-1,8-naphthalic anhydride is 4-bromo-1,8-naphthalic anhydride and wherein said at least one etheramine is represented by the formula (II):

$$R_3\text{—}O\text{—}(CH_2)_3NH_2 \qquad (II)$$

wherein $R_3$ is a ($C_1$–$C_{30}$ branched or unbranched) alkyl group.

* * * * *